(12) United States Patent
Liphardt et al.

(10) Patent No.: US 8,436,994 B2
(45) Date of Patent: *May 7, 2013

(54) FAST SAMPLE HEIGHT, AOI AND POI ALIGNMENT IN MAPPING ELLIPSOMETER OR THE LIKE

(75) Inventors: Martin M. Liphardt, Lincoln, NE (US); Jeffrey S. Hale, Lincoln, NE (US); Ping He, Lincoln, NE (US); Galen L. Pfeiffer, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 245 days.

This patent is subject to a terminal disclaimer.

(21) Appl. No.: 12/930,762

(22) Filed: Jan. 15, 2011

(65) Prior Publication Data
US 2011/0109906 A1 May 12, 2011

Related U.S. Application Data

(60) Continuation-in-part of application No. 12/313,760, filed on Nov. 25, 2008, now Pat. No. 7,872,751, which (Continued)

(60) Provisional application No. 61/127,062, filed on May 9, 2008, provisional application No. 60/836,232, filed on Aug. 9, 2006, provisional application No. 60/580,314, filed on Jun. 17, 2004, provisional application No. 60/564,747, filed on Apr. 23, 2004, provisional application No. 60/287,784, filed on May 2, 2001, provisional application No. 60/263,874, filed on Jan. 25, 2001, provisional application No. 60/261,243, filed on Jan. 16, 2001, provisional application No. 60/480,851, filed on Jun. 24, 2003, provisional application No. 60/427,043, filed on Nov. 18, 2002, provisional application No. 60/424,589, filed on Nov. 7, 2002, provisional application No. 60/772,926, filed on Feb. 13, 2006, provisional application No. 60/300,714, filed on Jun. 26, 2001, provisional application No. 60/431,489, filed on Dec. 6, 2002, provisional application No. 60/878,799, filed on Jan. 5, 2007.

(51) Int. Cl.
*G01J 4/00* (2006.01)

(52) U.S. Cl.
USPC ............................ 356/364; 356/399; 356/400

(58) Field of Classification Search .................. 356/364, 356/399
See application file for complete search history.

(56) References Cited

U.S. PATENT DOCUMENTS

| | | | |
|---|---|---|---|
| 3,874,797 A | 4/1975 | Kasai | 356/369 |
| 4,647,207 A | 3/1987 | Bjork et al. | 356/369 |

(Continued)

OTHER PUBLICATIONS

"Regression Calibration Method for Rotwing Element Ellipsometers," John, Thin Film Solds, vol. 234, (1993).

*Primary Examiner* — Layla Lauchman
(74) *Attorney, Agent, or Firm* — James D. Welch

(57) ABSTRACT

A sample investigation system (ES) in functional combination with an alignment system (AS), and methodology of enabling calibration and very fast, (eg. seconds), sample height, angle-of-incidence and plane-of-incidence adjustments, with application in mapping ellipsometer or the like systems.

7 Claims, 7 Drawing Sheets

Related U.S. Application Data is a continuation-in-part of application No. 11/890,391, filed on Aug. 5, 2007, now Pat. No. 7,746,471, said application No. 12/313,760 is a continuation-in-part of application No. 11/105,852, filed on Apr. 14, 2005, now Pat. No. 7,277,171, said application No. 12/313,760 is a continuation-in-part of application No. 10/829,620, filed on Apr. 22, 2004, now Pat. No. 7,193,710, and a continuation-in-part of application No. 10/925,333, filed on Aug. 24, 2004, now Pat. No. 7,265,838, and a continuation-in-part of application No. 10/050,802, filed on Jan. 15, 2002, now Pat. No. 6,859,278, and a division of application No. 10/050,802, said application No. 12/313,760 is a continuation-in-part of application No. 10/699,540, filed on Nov. 1, 2003, now Pat. No. 7,158,231, and a continuation-in-part of application No. 10/857,774, filed on May 28, 2004, now Pat. No. 7,274,450, said application No. 12/313,760 is a continuation-in-part of application No. 11/704,545, filed on Feb. 10, 2007, now Pat. No. 7,426,030, said application No. 12/313,760 is a continuation-in-part of application No. 11/145,470, filed on Jun. 6, 2005, now Pat. No. 7,327,456, and a continuation-in-part of application No. 10/376,677, filed on Feb. 28, 2003, now Pat. No. 6,982,792, and a continuation-in-part of application No. 09/531,877, filed on Mar. 21, 2000, now Pat. No. 6,535,286, and a continuation-in-part of application No. 10/178,723, filed on Jun. 24, 2002, now Pat. No. 6,950,182, and a continuation-in-part of application No. 09/583,229, filed on May 30, 2000, now Pat. No. 6,804,004, and a continuation-in-part of application No. 09/864,840, filed on May 24, 2001, now Pat. No. 6,456,376, and a continuation-in-part of application No. 09/845,548, filed on Apr. 30, 2001, now Pat. No. 6,585,128, said application No. 12/313,760 is a continuation-in-part of application No. 10/849,740, filed on May 20, 2004, now Pat. No. 7,385,697, said application No. 11/704,545 is a continuation-in-part of application No. 11/105,852, and a continuation-in-part of application No. 10/829,620, and a continuation-in-part of application No. 10/925,333, and a division of application No. 10/050,802, and a continuation-in-part of application No. 10/925,333, which is a continuation-in-part of application No. 10/829,620, which is a division of application No. 10/050,802, said application No. 12/313,760 is a continuation-in-part of application No. 11/784,750, filed on Apr. 10, 2007, now Pat. No. 7,567,345.

(56) References Cited

U.S. PATENT DOCUMENTS

| | | | |
|---|---|---|---|
| 4,672,196 A | 6/1987 | Canino | 250/225 |
| 5,343,293 A | 8/1994 | Berger et al. | 356/369 |
| 5,410,409 A | 4/1995 | Ray | 356/369 |
| 5,412,473 A | 5/1995 | Rosencwaig et al. | 356/451 |
| 5,581,350 A | 12/1996 | Chen et al. | 356/369 |
| 5,764,365 A | 6/1998 | Finarov | 356/630 |
| 6,081,334 A | 6/2000 | Grimbergen et al. | 356/499 |
| RE38,153 E | 6/2003 | Finarov | 356/630 |
| 6,678,043 B1 | 1/2004 | Vurens | 356/237.2 |
| 7,099,010 B2 | 8/2006 | Schulz | 356/401 |
| 7,295,330 B2 | 11/2007 | Chow | 356/630 |
| 7,327,444 B2 | 2/2008 | Naka et al. | 356/73 |
| RE40,225 E | 4/2008 | Finarov | 356/630 |
| 7,872,751 B2 * | 1/2011 | Liphardt et al. | 356/364 |

* cited by examiner

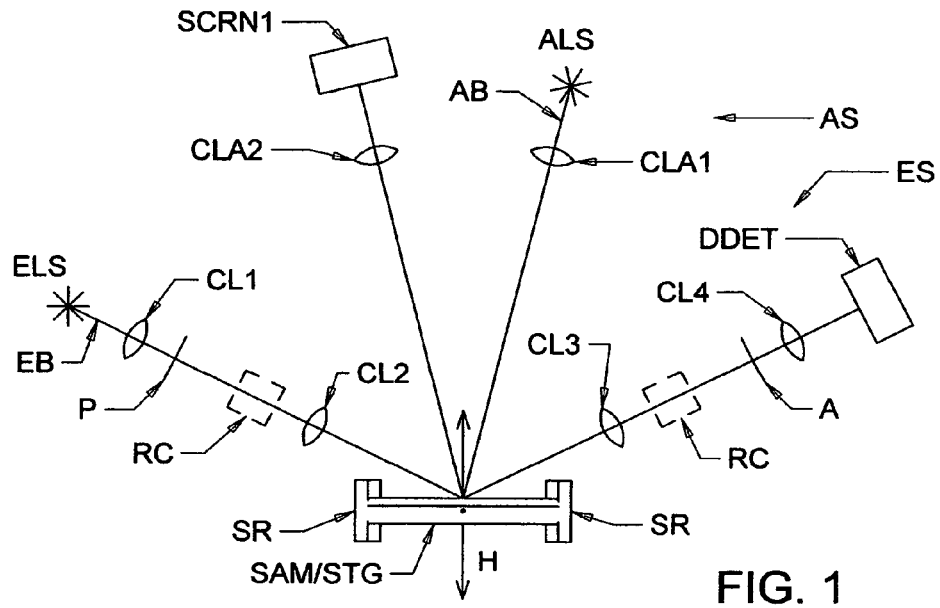
FIG. 1
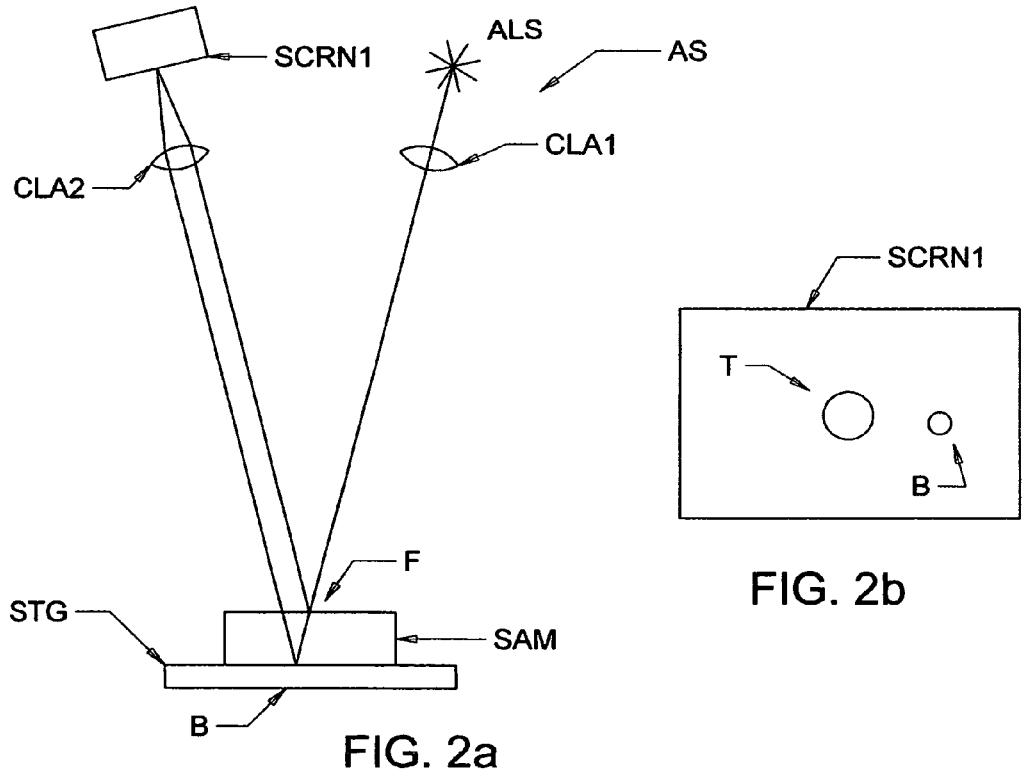
FIG. 2a
FIG. 2b

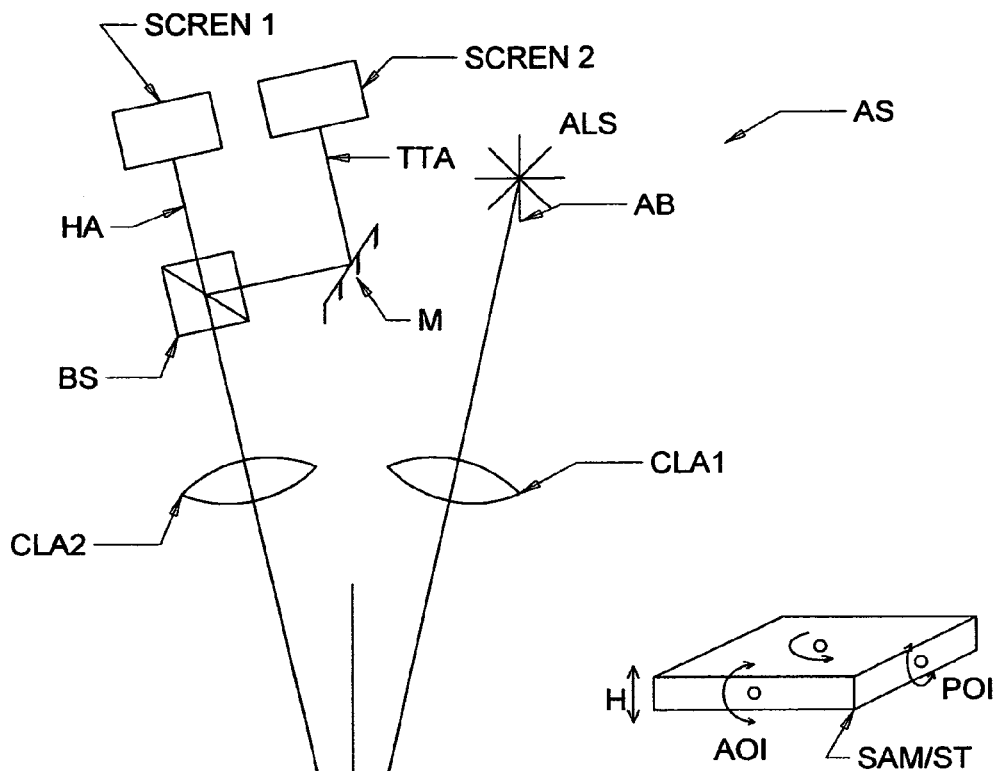
FIG 3a
FIG. 3b
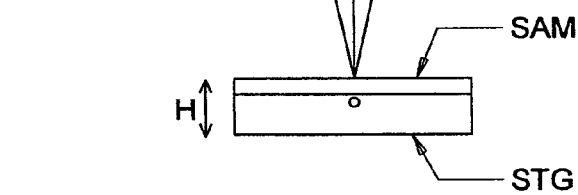
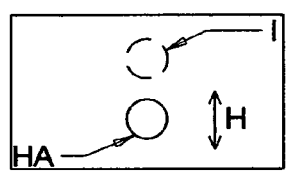
FIG. 3c
FIG. 3d

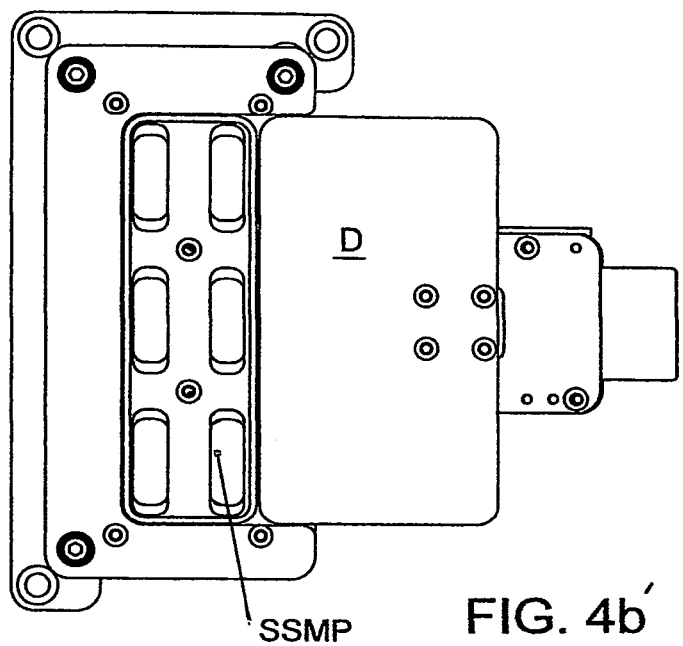
FIG. 4b'
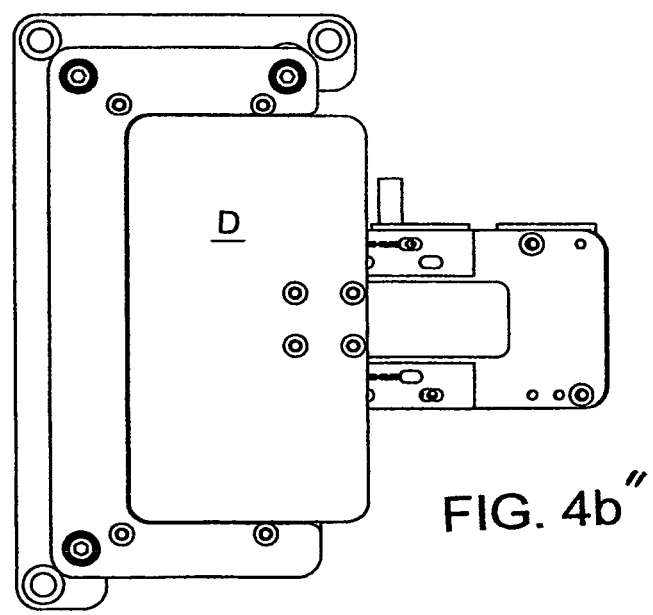
FIG. 4b"

FAST SAMPLE HEIGHT, AOI AND POI ALIGNMENT IN MAPPING ELLIPSOMETER OR THE LIKE

This Application is a CIP of application Ser. No. 12/313,760 Filed Nov. 25, 2008 and therevia of Claims Benefit of Provisional Application Ser. No. 61/127,062 Filed May 9, 2008. Via application Ser. No. 12/313,760, this Application is a CIP of application Ser. No. 11/890,391 Filed Aug. 5, 2007 and therefrom Claims benefit of Provisional 60/836,232 Filed Aug. 9, 2006, and therevia is a CIP of Pending patent application Ser. No. 11/105,852 filed Apr. 14, 2005, and therevia this Application Claims benefit of Provisional Applications 60/564,747 Filed Apr. 23, 2004, and 60/580,314 Filed Jun. 17, 2004. This Application is further a Continuation-In-Part of Utility application Ser. Nos. 10/829,620 Filed Apr. 22, 2004; and of 10/925,333 Filed Aug. 24, 2004, and therevia of 10/050,802 Filed Jan. 15, 2002, (now U.S. Pat. No. 6,859,278). Via the above Applications this Application is further a Continuation-In-Part of Utility application Ser. Nos. 10/925,333 Filed Aug. 24, 2004, and of 10/829,620 Filed Apr. 22, 2004, and is a Divisional of 10/050,802 Filed Jan. 15, 2002; and via the above Applications Claims Benefit of Provisional Application Ser. Nos. 60/261,243 Filed Jan. 16, 2001, 60/263,874 Filed Jan. 25, 2001, 60/287,784 Filed May 2, 2001. This Application is further a CIP of Utility application Ser. Nos. 10/699,540 Filed Nov. 1, 2003, and 10/857,774 Filed May 28, 2004, and therevia Claims benefit of Provisional Applications 60/424,589 Filed Nov. 7, 2002, 60/427,043 Filed Nov. 18, 2002, and 60/480,851 Filed Jun. 24, 2003. This Application is further directly a CIP of Pending application Ser. No. 11/704,545 Filed Feb. 10, 2007 and therevia Claims Benefit of Provisional Application Ser. No. 60/772,926 Filed Feb. 13, 2006; and is a CIP of Co-Pending application Ser. No. 11/145,470 Filed Jun. 6, 2005, and therevia of Ser. No. 10/376,677 Filed Feb. 28, 2003 and from Ser. Nos. 09/531,877 Filed Mar. 21, 2000; and from 10/178,723 filed Jun. 24, 2002; and 09/583,229 filed May 30, 2000; and from 09/864,840 filed May 24, 2001; and 09/845,548 filed May 14, 2001; and Claims benefit of Provisional Application Serial Nos. 60/300,714 filed Jun. 26, 2001, and 60/424,589 filed Nov. 7, 2002, and 60/427,043 filed Nov. 18, 2002 and 60/431,489 filed Dec. 6, 2002. This Application also is a CIP of Co-Pending application Ser. No. 10/849,740 Filed May 20, 2004. This Application is also a CIP of Pending application Ser. No. 11/105,852 Filed Apr. 14, 2005 also therevia Claims benefit of Provisional Applications 60/564,747 Filed Apr. 23, 2004, and 60/580,314 Filed Jun. 17, 2004. This Application is further a Continuation-In-Part of Utility application Ser. Nos. 10/829,620 Filed Apr. 22, 2004; and of 10/925,333 Filed Aug. 24, 2004, and therevia of 10/050,802 Filed Jan. 15, 2002, (now U.S. Pat. No. 6,859,278). This Application is further a Continuation-In-Part of Utility application Ser. Nos. 10/925,333 Filed Aug. 24, 2004, and of 10/829,620 Filed Apr. 22, 2004, and is a Divisional of 10/050,802 Filed Jan. 15, 2002; and via the above Applications Claims Benefit of Provisional Application Ser. Nos. 60/261,243 Filed Jan. 16, 2001, 60/263,874 Filed Jan. 25, 2001, 60/287,784 Filed May 2, 2001.

This Application also is a CIP from application Ser. No. 11/784,750 Filed Apr. 10, 2007, and therevia from Provisional Application 60/878,799 Filed Jan. 5, 2007.

TECHNICAL AREA

The present invention relates to the practice of ellipsometry, polarimetry, reflectometry and spectrophotometry; and more particularly to a sample investigation system and method of enabling very fast sample height, angle-of-incidence and plane-of-incidence adjustments, with application in a sample mapping or the like systems.

BACKGROUND

Ellipsometry is a well known approach to determining physical and optical properties of samples. To obtain accurate results, however, requires that values for certain adjustable parameters, including the distance between the ellipsometer and the sample under investigation, (eg. the "height" of the sample), and the angle-of-incidence and plane-of-incidence of the ellipsometer beam with respect to the sample, be known. Where single point on a sample is to be investigated, alignment procedures are well established which provide the required values within acceptable time constraints, (eg. many seconds to a minute or so). However, in situations wherein many points on a large sample, (eg. a mapping of the sample is to be performed), the time required to do conventional alignments at each of the many point investigated can introduce unacceptable, (eg. 5 seconds each), time delays in achieving desired results. The present invention provides an alignment system, and method of its use, which enables very fast, (eg. on the order a second or two), setting of sample height, and angle, and plane-of-incidence, at each spot on the sample to be investigated. The present invention also discloses a relevant sample mapping system which applies the alignment system.

As further insight, it is noted that Pending patent application Ser. No. 11/890,391 Filed Aug. 5, 2007 provides priority back to application Ser. No. 11/105,852, Filed Apr. 14, 2005, with Priority back to Apr. 23, 2004 via Provisional Application Ser. No. 60/564,747, and describes a substantially self contained flying ellipsometer, polarimeter, reflectometer or spectrophotometer system that provides for moving a combined source and detector of electromagnetic radiation over the a surface of a sample in two, (eg. "X" and "Y"), orthogonal dimensions to enable positioning it at desired locations on, and offset distance from sample in a "Z" dimension corresponding to a distance between said combined source and detector and said sample, and which enables easy sequential setting of different Angles-of-Incidence of a beam of electromagnetic radiation to a surface of said sample.

As related in the 391 Pending Application, Ellipsometer Systems generally include a source of a beam of electromagnetic radiation, a Polarizer, which serves to impose a known, (typically linear), state of polarization on a beam of electromagnetic radiation, a Stage for supporting a sample, and an Analyzer which serves to select a polarization state in a beam of electromagnetic radiation after it has interacted with a material system, and pass it to a Detector System for analysis therein. As well, one or more Compensator(s) can be present and serve to affect a phase retardance between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because they do not demonstrate "Dead-Spots" where obtaining ellipsometric data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have a "Dead Spot" at PSI near 45 Degrees). The utility of Rotating Compensator Ellipsometer Systems should then be apparent. Another benefit provided by Rotating Compensator Ellipsometer Systems is that the Polarizer (P) and Analyzer (A) positions are fixed, and that provides benefit in that polarization state sensitivity to input and output optics during data acquisition is essentially non-existent. This enables relatively easy use of optic fibers, mirrors, lenses etc. for input/output.

Typical construction of spectrophotometer, reflectometer, polarimeter, ellipsometer and the like systems, (eg. Rotating Analyzer, Rotating Polarizer, Rotating Compensator, Modulator Element Ellipsometer), provides a Sample Supporting Stage which is substantially fixed in location. Functionally oriented with respect thereto are a Substantially Fixed Position Source Means (S) for providing a beam of electromagnetic radiation at an oblique angle to said Sample Supporting Stage, and a Substantially Fixed Position Data Detector Means (D) for intercepting Electromagnetic Radiation which Reflects (or Transmits through), a Sample placed on said Sample Supporting Stage. Typical procedure is to place a Sample onto the Sample Supporting Stage, cause a beam of Electromagnetic Radiation to impinge thereonto, and record data produced by the Data Detector Means in response to electromagnetic radiation which enters thereinto, which data is analyzed to provide insight into Sample Optical and Physical properties. Said procedure can include adjustment of the Sample Supporting Stage, or the source and detector of electromagnetic radiation in an "X"-"Y" Plane, and along a "Z" direction perpendicular to its surface, (ie. a vertical position adjustment where the Electromagnetic Radiation approaches the Sample at an oblique angle from a laterally located Source). This purpose of said "Z" adjustment is, for instance, to enable the directing of a beam of Electromagnetic Radiation Reflected from a Sample placed on said Sample Supporting Stage into the Data Detector without moving the Data Detector so it intercepts a beam exiting said Sample. It should be appreciated then that conventional Reflectometer, Ellipsometer and Polarimeter Systems which include provision for such Sample positioning adjustment and orientation with respect to an impinging Electromagnetic beam, typically do so by allowing the Sample Supporting Stage position to be adjusted, rather than by effecting simultaneous change in location of the Source and Data Detector with respect to the Sample Supporting Stage, because it is far simpler to implement Sample Supporting Stage location change. However, an alternative is mount a Reflectometer, Spectrophotometer, Ellipsometer, Polarimeter or the like System to a means for moving it in an "X"-"Y" Plane, and along a "Z" direction perpendicular to its surface of the Sample with respect to a substantially fixed position Stage for supporting a Sample. In either case, however, a relative motion occurs between the Reflectometer, Ellipsometer, Polarimeter or the like System and a sample.

The present invention then breaks with conventional practice by, while typically providing a substantially fixed position Stage for supporting a Sample, providing a Reflectometer, Spectrophotometer, Ellipsometer, Polarimeter or the like System which is mounted to a positioning system which allows adjustment its location in an "X"-"Y" Plane, and along a "Z" direction perpendicular to its surface of the Sample. The present invention then, allows investigation of a large Sample at many locations thereof.

Continuing, while present invention systems can be applied in any material system investigation system such as Polarimeter, Reflectometer, Spectrophotometer and the like Systems, an important application is in Ellipsometer Systems, whether monochromatic or spectroscopic. It should therefore be understood that Ellipsometry involves acquisition of sample system characterizing data at single or multiple Wavelengths, and at one or more Angle(s)-of-Incidence (AOI) of a Beam of Electromagnetic Radiation to a surface of the sample system.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system:

$$TAN(\psi)e^{(i\Delta)} = r_p/r_s$$

While Data taken at one (AOI) and one or multiple wavelengths is often sufficient to allow ellipsometric characterization of a sample system, the results of Ellipsometric Investigation can be greatly enhanced by using multiple (AOI's) to obtain additional data sets. However, while it is relatively easy to provide Wavelength change without extensive difficult physical Ellipsometer System Orientation change, it is typically difficult to change the Angle-of-Incidence (AOI) that a Beam of Electromagnetic Radiation makes to a surface of a sample system. An (AOI) change requires that both the Source of the Electromagnetic Beam and the Detector must be re-positioned and aligned, and such is tedious and time consuming. The present invention therefore can provide means to easily effect (AOI) change. It is also noted that ellipsometric data is typically analyzed by proposing a mathematical model for the sample and regressing it on to said ellipsometric data to arrive at values for parameters in the mathematical model which meet, for instance, a best fit based on a least square error criteria. Further, it is known to obtain data from multiple similar samples and simultaneously regress the similar models onto the different ellipsometric data sets. This technique can break correlation between thickness and refractive index, where the samples have different thicknesses. A similar approach can be applied to data acquired from multiple spots on a single sample.

A Patent to Finarov, U.S. Pat. No. 5,764,365 is disclosed as it describes a system for moving an ellipsometer beam over a large two-dimensional area on the surface of a sample system, which system utilizes beam deflectors.

A Patent to Berger et al., U.S. Pat. No. 5,343,293 describes an Ellipsometer which comprises prisms to direct an electromagnetic beam onto a sample system.

A Patent to Canino, U.S. Pat. No. 4,672,196 describes a system which allows rotating a sample system to control the angle of incidence of a beam of electromagnetic radiation thereonto. Multiple detectors are present to receive the resulting reflected beams.

A Patent to Bjork et al., U.S. Pat. No. 4,647,207 describes an ellipsometer system in which reflecting elements are moved into the path of a beam of electromagnetic radiation.

U.S. Pat. No. 6,081,334 to Grimbergen et al. describes a system for detecting semiconductor end point etching including a means for scanning a beam across the surface of a substrate.

A Patent to Ray, U.S. Pat. No. 5,410,409 describes a system for scanning a laser beam across a sample surface.

U.S. Pat. No. 3,874,797 to Kasai describes means for directing a beam of electromagnetic radiation onto the surface of a sample using totally internally reflecting prisms.

U.S. Pat. No. 5,412,473 to Rosencwaig et al., describes a ellipsometer system which simultaneously provides an electromagnetic beam at a sample surface at numerous angles of incidence thereto.

A Patent to Chen et al., U.S. Pat. No. 5,581,350 is identified as it describes the application of regression in calibration of ellipsometer systems.

A Search of Patents which contain both "ellipsometer" and "Mapping" provided Patents Nos.:
RE40,225 to Finarov;
RE38,153 to Finarov;
U.S. Pat. No. 6,678,043 to Vurens;
U.S. Pat. No. 7,099,010 to Schulz;
U.S. Pat. No. 7,295,330 to Chow;
U.S. Pat. No. 7,327,444 to Naka et al.

An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration.

Even in view of the prior art, need remains for:
an ellipsometer system which enables very fast, (eg. on the order a second or two), setting of sample height, and angle, and plane-of-incidence, at each spot on the sample to be investigated and a sample mapping system which applies the alignment system; and
an ellipsometer system which is functionally mounted in a three dimension location means for positioning said selected system at points in a three dimensional setting, including rotational capability.

DISCLOSURE OF THE INVENTION

As presented in parent application Ser. No. 12/313,760, a previously disclosed embodiment of a present invention comprises a method of aligning a sample in an ellipsometer system. Said ellipsometer system can be described as comprising:
a source of a beam of electromagnetic radiation;
a polarizer;
a stage for supporting a sample;
an analyzer;
a data detector;
means for adjusting the relative "height" positioning between said stage for supporting a sample and, as a unit, said source of a beam of electromagnetic radiation and data detector; as well as means for translating relative positioning of said sample with respect to said source of an ellipsometer beam of electromagnetic radiation and said data detector, along two orthogonal axes, and optionally means for adjusting the relative orientation of the ellipsometer systems with respect to said sample to set the angle and plane of incidence of said ellipsometer beam with respect to a surface of said sample.

Said ellipsometer system can comprise at least one compensator and/or focusing means between said source of a beam of electromagnetic radiation and said data detector.

In use a beam of electromagnetic radiation from said source thereof approaches said sample at an oblique angle-of-incidence and reflects therefrom into said data detector.

Said method of aligning a sample further comprises the steps of:

a) functionally mounting a sample alignment system to said ellipsometer system, which sample alignment system comprises:
an alignment source of an alignment beam of electromagnetic radiation;
a first alignment beam focusing means for focusing an alignment beam of electromagnetic radiation provided from said source thereof onto a sample on said ellipsometer system stage for supporting a sample;
a second alignment focusing means for focusing alignment beam electromagnetic radiation which reflects from said sample onto a two dimensional detector array; and
said two dimensional detector array;
such that in use an alignment beam of electromagnetic radiation from said source thereof is focused onto said sample at an oblique angle-of-incidence and reflects therefrom and is focused onto said two dimensional detector array.

Said sample alignment system can optionally further comprise:
between said second alignment focusing means and said two dimensional detector array a beam splitter which diverts a portion of the alignment beam electromagnetic radiation which reflects from said sample to a secondary two dimensional detector array, and said secondary two dimensional detector array.

Said ellipsometer and alignment system are mounted with respect to one another such that the ellipsometer beam of electromagnetic radiation and said alignment beam of electromagnetic radiation impinge on said sample at substantially the same location.

Said method further can also comprise:
prior to step e, performing steps b and c at least once, said steps b and c being:
b) while:
monitoring output intensity from said data detector causing a beam of electromagnetic radiation from said source thereof to approach said sample at an oblique angle-of-incidence and reflect therefrom into said data detector,
adjusting the means for adjusting the relative "height" positioning between said stage for supporting a sample, and, as a unit, said source of a beam of electromagnetic radiation and data detector, until output from said data detector is of a desirable intensity; and
c) causing the source of an alignment beam of electromagnetic radiation from said source thereof to approach said sample at an oblique angle-of-incidence and reflect therefrom onto said two dimensional detector array and identifying the location on said two dimensional detector array as an aligned position.

Said method can then further comprise performing steps d, e and f a plurality of times, said steps d, e and f being:
d) using said means for translating relative positioning of said sample with respect to, as a unit, said source of an ellipsometer beam of electromagnetic radiation and said data detector, along two orthogonal axes, causing relative translation of said sample along at least one of said orthogonal axes so that a new spot on said sample is investigated by said ellipsometer beam, and such that the location at which the alignment beam reflected from said sample surface in step c appears on the two dimensional detector array, possibly at a different location than said aligned position;
e) if necessary, adjusting the means for adjusting the relative "height" positioning between said stage for supporting a sample and, as a unit, said source of a beam of electromagnetic radiation and data detector, until said alignment beam reflected from said sample surface in step c appears on the two dimensional detector array at said aligned position;

f) with the above adjustment set, acquiring ellipsometric data from said data detector.

Said method can further comprise definitely providing:

between said second alignment focusing means and said two dimensional detector array, a beam splitter which diverts a portion of the alignment beam electromagnetic radiation which reflects from said sample to a secondary two dimensional detector array and said secondary two dimensional detector array; and means for adjusting the relative orientation of the ellipsometer with respect to said sample to set the angle and plane of incidence of said ellipsometer beam with respect to a surface of said sample.

Said method can then further comprise, prior to step e:

while causing a beam of electromagnetic radiation from said source thereof to approach said sample at an oblique angle-of-incidence and reflect therefrom into said data detector, monitoring the output from the data detector and adjusting the means for adjusting the relative orientation of the ellipsometer with respect to said sample to set the angle and plane of incidence of said ellipsometer beam with respect to a surface of said sample until the intensity of the data detector output is maximized, and so that electromagnetic radiation from said alignment source thereof reflects from said sample and, via said beam splitter, appears on said secondary two dimensional detector array, and identifying the location on said secondary two dimensional detector array as an aligned position;

and in which said method, after practice of the step d causing of relative translation of said sample along at least one of said orthogonal axes so that a new spot on said sample is investigated by said ellipsometer beam, practice of step e, which step e further comprises:

e) adjusting the means for adjusting the relative orientation of the ellipsometer with respect to said sample to set the angle and plane of incidence of said ellipsometric beam with respect to a surface of said sample until said alignment beam reflected from said sample surface in step c appears on the two dimensional detector array at said aligned position;

followed by practice of step f.

A more comprehensive recitation of the method of aligning a sample in an ellipsometer system comprises, providing an ellipsometer system which comprises:

a source of a beam of electromagnetic radiation;
a polarizer;
a stage for supporting a sample;
an analyzer;
a data detector;
means for adjusting the relative "height" positioning between said stage for supporting a sample and, as a unit, said source of a beam of electromagnetic radiation and data detector; as well as means for translating relative positioning of said sample with respect to said source of an ellipsometer beam of electromagnetic radiation and said data detector, along two orthogonal axes, and means for adjusting the relative orientation of the ellipsometer with respect to said sample to set the angle and plane of incidence of said ellipsometer beam with respect to a surface of said sample.

Said system optionally can comprise at least one polarizer, analyzer, compensator or focusing means between said source of a sample investigation beam of electromagnetic radiation and said data detector.

In use a beam of electromagnetic radiation from said source thereof approaches said sample at an oblique angle-of-incidence and reflects therefrom into said data detector.

Said method also comprises the steps of:

a) functionally mounting a sample alignment system to said ellipsometer system, which sample alignment system comprises:

an alignment source of an alignment beam of electromagnetic radiation;

a first alignment beam focusing means for focusing an alignment beam of electromagnetic radiation provided from said source thereof onto a sample on said ellipsometer system stage for supporting a sample;

a second alignment focusing means for focusing alignment beam electromagnetic radiation which reflects from said sample onto a two dimensional detector array; and said two dimensional detector array, such that in use an alignment beam of electromagnetic radiation from said source thereof is focused onto said sample at an oblique angle-of-incidence and reflects therefrom and is focused onto said two dimensional detector array.

Said sample alignment system further comprises:

between said second alignment focusing means and said two dimensional detector array, a beam splitter which diverts a portion of the alignment beam electromagnetic radiation which reflects from said sample to a secondary two dimensional detector array, and said secondary two dimensional detector array;

said ellipsometer and alignment system being mounted with respect to one another such that the ellipsometer beam of electromagnetic radiation and said alignment beam of electromagnetic radiation impinge on said sample at substantially the same location.

Said method then further comprises, prior to step e, performing steps b and c at least once, said steps b an c being:

b) while causing a beam of electromagnetic radiation from said source thereof to approach said sample at an oblique angle-of-incidence and reflect therefrom into said data detector, monitoring the output from the data detector and adjusting the means for adjusting the relative orientation of the ellipsometer with respect to said sample to set the angle and plane of incidence of said ellipsometer beam with respect to a surface of said sample until the intensity of the data detector output is maximized, and so that electromagnetic radiation from said alignment source thereof reflects from said sample and, via said beam splitter, appears on said secondary two dimensional detector array, and identifying the location on said secondary two dimensional detector array as an aligned position; and c) while monitoring output intensity from said data detector causing a beam of electromagnetic radiation from said source thereof to approach said sample at an oblique angle-of-incidence and reflect therefrom into said data detector adjusting the means for adjusting the relative "height" positioning between said stage for supporting a sample, and, as a unit, said source of a beam of electromagnetic radiation and data detector until output from said data detector is of a desirable intensity and identifying the location on said two dimensional detector array as an aligned position.

Said method then further comprises performing steps d, e and f a plurality of times, said steps d, e and f being:

d) using said means for translating relative positioning of said sample with respect to, as a unit, said source of an ellipsometer beam of electromagnetic radiation and said data detector, along two orthogonal axes, causing relative translation of said sample along at least one of said orthogonal axes so that a new spot on said sample is investigated by said ellipsometer beam, and such that the location at which the alignment beam reflected from said sample surface in step c appears on the two dimensional detector array, possibly at a different location than said aligned position;

e) if necessary, adjusting the means for adjusting the relative "height" positioning between said stage for supporting a sample and, as a unit, said source of a beam of electromagnetic radiation and data detector, until said alignment beam reflected from said sample surface in step c appears on the two dimensional detector array at said aligned position and adjusting the means for adjusting the relative orientation of the ellipsometer with respect to said sample to set the angle and plane of incidence of said ellipsometric beam with respect to a surface of said sample until said alignment beam reflected from said sample surface in step c appears on the secondary two dimensional detector array at said aligned position;

f) with the above adjustment set, acquiring ellipsometric data from said data detector.

In the foregoing it is noted that steps b and c are practiced "at least once", while steps d, e and f are practiced "a plurality of times". This language is used to indicate that while step c, and optionally step b, could be practiced every time steps d, e and f are practiced at a location on a sample, it is often sufficient to practice steps c, (and optionally b), only once each followed by practice of steps d, e and f many times. This is because the sample can be sufficiently planar so that setting height, angle and plane of incidence once, for many locations thereupon, can be sufficient. Hence, while the methodology can involve practicing step c, and optionally step b, each time steps d, e and f are practiced, typically this will not be the case.

Present invention methodology of investigating a sample can further comprise analyzing ellipsometric data acquired from said data detector in step f, and that analysis can involve the acquiring of ellipsometric data involves repeating steps b-f at least twice to obtain ellipsometric data from at least two spots on said sample, and in which the analysis comprises simultaneous regression onto data obtained from said at least two spots on said sample.

It is also noted that steps wherein relative "height" positioning between said stage for supporting a sample and, as a unit, is involved, the data detector output is set to be of a "desirable intensity". This is to indicate that it need not be "maximized". However, where relative orientation of the ellipsometer with respect to said sample to set the angle and plane of incidence of said ellipsometer beam with respect to a surface of said sample is involved, maximizing the data detector output is practiced. This is because if said angle and/or plane of incidence is not set to direct a beam into the data detector no data detector output is obtained and the range over which a signal is detected is small. That is, the adjustment for the angle and plane of incidence is critical within tight limits in order to obtain data at all, whereas the height adjustment does not have such tight limits. Practice might include "maximizing" the data detector output while adjusting for height, but said maximization need not in the present invention.

Methodology herein can also involve performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

While the foregoing discussed the very relevant application of an exemplary ellipsometer system, the Claims should be broadly considered to involve any material system investigation system, such as:

an ellipsometer;
a polarimeter;
a reflectometer;
a spectrophotometer; and
a Mueller Matrix measuring system.

In that light, the present invention can be recited as also comprising a combination sample investigation system and alignment system comprising a selection from the group consisting of:

an ellipsometer;
a polarimeter;
a reflectometer;
a spectrophotometer; and
a Mueller Matrix measuring system;

which comprises:

a source of a sample investigation beam of electromagnetic radiation;
a stage for supporting a sample;
a data detector;
means for adjusting the relative "height" positioning between said stage for supporting a sample and, as a unit, said source of a sample investigation beam of electromagnetic radiation and data detector; as well as, optionally, means for translating relative positioning of said sample with respect to said source of a sample investigation beam of electromagnetic radiation and said data detector, along two orthogonal axes, and optionally means for adjusting the relative orientation of the sample investigation system with respect to said sample to set the angle and plane of incidence of said sample investigation beam of electromagnetic radiation with respect to a surface of said sample.

Said system optionally can comprise at least one polarizer, analyzer, compensator or focusing means between said source of a sample investigation beam of electromagnetic radiation and said data detector.

In use a sample investigation beam of electromagnetic radiation from said source thereof approaches said sample at an oblique angle-of-incidence and reflects therefrom into said data detector.

Said sample investigation system optionally comprises an alignment system which comprises:

an alignment source of an alignment beam of electromagnetic radiation;
a first alignment beam focusing means for focusing an alignment beam of electromagnetic radiation provided from said source thereof onto a sample on said ellipsometer system stage for supporting a sample;
a second alignment focusing means for focusing alignment beam electromagnetic radiation which reflects from said sample onto a two dimensional detector array; and
said two dimensional detector array;
such that in use an alignment beam of electromagnetic radiation from said source thereof is focused onto said sample at an oblique angle-of-incidence and reflects therefrom and is focused onto said two dimensional detector array.

Said sample alignment system optionally further comprises:
between said second alignment focusing means and said two dimensional detector array a beam splitter which diverts a portion of the alignment beam electromagnetic radiation which reflects from said sample to a secondary two dimensional detector array, and said secondary two dimensional detector array;
said sample investigation system and alignment system being mounted with respect to one another such that the sample investigation beam of electromagnetic radiation and said alignment beam of electromagnetic radiation impinge on said sample at substantially the same location.

Said combination sample investigation system and alignment system can further comprise:
a mounting frame which supports said combination sample investigation system, and alignment system, said mounting frame projecting vertically upward from a horizontally oriented support as viewed in elevation, and having affixed thereto said means for adjusting the relative "height" positioning between said stage for supporting a sample and, as a unit, said source of a beam of electromagnetic radiation and data detector, as well as said means for translating relative positioning of said sample with respect to said source of a beam of electromagnetic radiation and said data detector, along two orthogonal axes, and said optional means for adjusting the relative orientation of the ellipsometer with respect to said sample to set the angle and plane of incidence of said beam with respect to a surface of said sample;
and in which said stage for supporting a sample is oriented to secure a sample in a plane slightly offset from said vertically upward projected plane of said mounting frame so that a sample entered thereinto does not tend to fall back out thereof, said stage being of a construction to contact the edges of the sample only.

Further, said combination sample investigation system and alignment system can further comprise:
a plurality of clamp means at the edges of said stage whereat the sample contacts said stage and which secure the sample to the stage at said edges thereof to better secure said sample, and to decrease non-planar warping therein.

ADDITIONAL DISCLOSURE

The presently disclosed invention comprises a sample alignment system (AS) in functional combination within a sample investigation system (ES) selected from the group consisting of:
ellipsometer;
polarimeter;
reflectometer;
spectrophotometer; and
Mueller Matrix measuring system;
said sample investigation system (ES) comprising:
a source (ELS) of a sample (SAM) investigation beam of electromagnetic radiation;
a stage (STG) for supporting a sample (SAM);
a data detector (DDET); and
means for adjusting the relative "height" positioning between said stage (STG) for supporting a sample (SAM) and, as a unit, said source (ELS) of a sample investigation beam of electromagnetic radiation and data detector (DDET); as well as means for translating relative positioning of said sample (SAM) with respect to said source (ELS) of a sample investigation beam of electromagnetic radiation and said data detector (DDET), along two orthogonal axes, and means for adjusting the relative orientation of the sample investigation system (ES) with respect to said sample (SAM) to set the angle and plane of incidence of said sample (SAM) investigation beam of electromagnetic radiation with respect to a surface of said sample (SAM).

Said sample investigation system (ES) can optionally comprises at least one polarizer (P), analyzer (A), compensator (RC) and/or focusing means (CL1) (CL2) (CL3) (CL4) between said source (ELS) of a sample (SAM) investigation beam of electromagnetic radiation and said data detector (DDET).

In use a sample investigation beam of electromagnetic radiation from said source (ELS) thereof approaches said sample (SAM) at an oblique angle-of-incidence and reflects therefrom into said data detector (DDET).

Said alignment system (AS) comprises:
an alignment source (ALS) of an alignment beam of electromagnetic radiation;
a first alignment beam focusing means (CLA1) for focusing an alignment beam of electromagnetic radiation provided from said source (ALS) thereof onto a sample (SAM) on said sample investigation system (ES) stage (STG) for supporting a sample (SAM);
a second alignment focusing means (CLA2) for focusing alignment beam electromagnetic radiation which reflects from said sample onto a two dimensional detector array (SCRN1); and
said two dimensional detector array (SCRN1).

Said sample alignment system (AS) further comprises:
between said second alignment focusing means (CLA2) and said two dimensional detector array (SCRN1), a beam splitter (BS) which diverts a portion of the alignment beam electromagnetic radiation which reflects from said sample (SAM) to a secondary two dimensional detector array (SCRN2), and said secondary two dimensional detector array (SCRN2).

In use an alignment beam of electromagnetic radiation from said source (ALS) thereof is focused onto said sample (SAM) at an oblique angle-of-incidence and reflects therefrom and is focused onto said two dimensional detector array (SCRN1) with a portion thereof being directed to secondary two dimensional detector array (SCRN2) via beam splitter (BS).

Said sample (SAM) investigation system (ES) and alignment system (AS) being mounted with respect to one another such that the sample investigation beam of electromagnetic radiation and said alignment beam of electromagnetic radiation impinge on said sample (SAM) at substantially the same location.

In use, while monitoring two dimensional detector array (SCRN1), an alignment beam of electromagnetic radiation from said source (ALS) thereof is caused to be focused onto said sample (SAM) at an oblique angle-of-incidence, reflect therefrom and become focused onto said two dimensional detector array (SCRN1), adjusting the means for adjusting the relative "height" positioning between said stage (STG) for supporting a sample until the location at which the alignment beam arrives thereat is at an aligned position thereupon; and such that in use the means for adjusting the relative orientation of the sample investigation system (ES) with respect to said sample (SAM), to set the angle and plane of incidence of said beam with respect to a surface of said sample (SAM) until said alignment beam reflected from said sample (SAM) surface appears on the two dimensional detector array (SCRN2) an aligned position thereupon.

Said sample alignment system can further comprise at least one known standard sample (SSMP) positioned away from said stage (STG) for supporting a sample (SAM), such that in use the sample investigation system (ES) and sample alignment system (AS) are positioned so that electromagnetic beams from each are directed to intereact with said at least one known standard sample (SSMP) while data is acquired from at least the sample investigation system (ES), followed by using said data to calibrate said sample investigation system (ES). And, said sample alignment system can also further comprises a door (D) which is applied the cover said at least one known standard sample (SSMP) when it is not in use, to prevent contamination thereof.

A method of investigating a plurality of locations on a sample comprises the steps of:
  a) providing a sample alignment system (AS) in functional combination within a sample investigation system (ES) as described just above;
  b) causing the sample investigation system (ES) and sample alignment system (AS) to be positioned such that electromagnetic beams from each are directed to intereact with said at least one known standard sample (SSMP) while data is acquired from at least the sample investigation system (ES), followed by using said data to calibrate said sample investigation system (ES);
  c) causing the sample investigation system (ES) and sample alignment system (AS) to be positioned such that electromagnetic beams from each are directed to intereact with a location on said sample (SAM) such that alignment beam of electromagnetic radiation from said source (ALS) of the sample alignment system is focused onto said sample (SAM) location at an oblique angle-of-incidence, reflects therefrom and is focused onto said two dimensional detector array (SCRN1) with a portion thereof being directed to secondary two dimensional detector array (SCRN2) via beam splitter (BS), followed by using information derived from screens (SCRN1) and (SCRN2), to adjust the distance between the sample (SAM) and said source (ELS) of a sample investigation beam of electromagnetic radiation and said data detector (DDET) as a unit, and to adjust the angle and plane of incidence of said sample (SAM) investigation beam of electromagnetic radiation with respect to a surface of said sample (SAM);
  d) acquiring data from said data detector (DDET) and therefrom deriving sample (SAM) characterizing information therefrom; and
  e) repeating steps c and d a plurality of times to provide (SAM) characterizing information at a plurality of locations thereupon.

Finally, it is noted that the Claims, in part, recite in some steps provide for setting data detector output of a "desirable intensity". This terminology is to be interpreted as including the possibility of causing a maximum possible intensity, but where not stated otherwise, not requiring such. For instance, this can be the case where prevention of detector saturation occurs when a maximum detector output occurs. Generally +/−20% maximum is "desirable".

The disclosed invention will be better understood by reference to the Detailed Description Section of this Disclosure, in combination with the Drawings.

BRIEF DESCRIPTION OF THE DRAWINGS

FIG. 1 shows a combination ellipsometer (ES) and alignment (AS) system.

FIG. 2a shows that a basic alignment system (AS).

FIG. 2b is included to show that beam components reflected from the front (F), and back (B), respectively, sides of the sample (SAM) can form two spots on the two dimensional detector array (SCRN1).

FIG. 3a shows a preferred sample alignment system (AS) which includes a beam splitter (BS) and a second two dimensional detector array (SCRN2).

FIG. 3b demonstrates that the (AOI) and (POI) of an ellipsometric beam (EB) can be adjusted with respect to a surface of said sample (SAM/STG) by rotation.

FIG. 3c shows that adjusting the height (H) between the sample (SAM) and the alignment system (AS), causes a movement of a spot (HA) on two dimensional detector array (SCRN1).

FIG. 3d shows that a relative tip/tilt between the sample (SAM) and the alignment system (AS) causes a spot (TTA) on the secondary two dimensional detector array (SCRN2) to move vertically with (AOI) and horizontally with (POI).

DETAILED DESCRIPTION

Figure 4A:
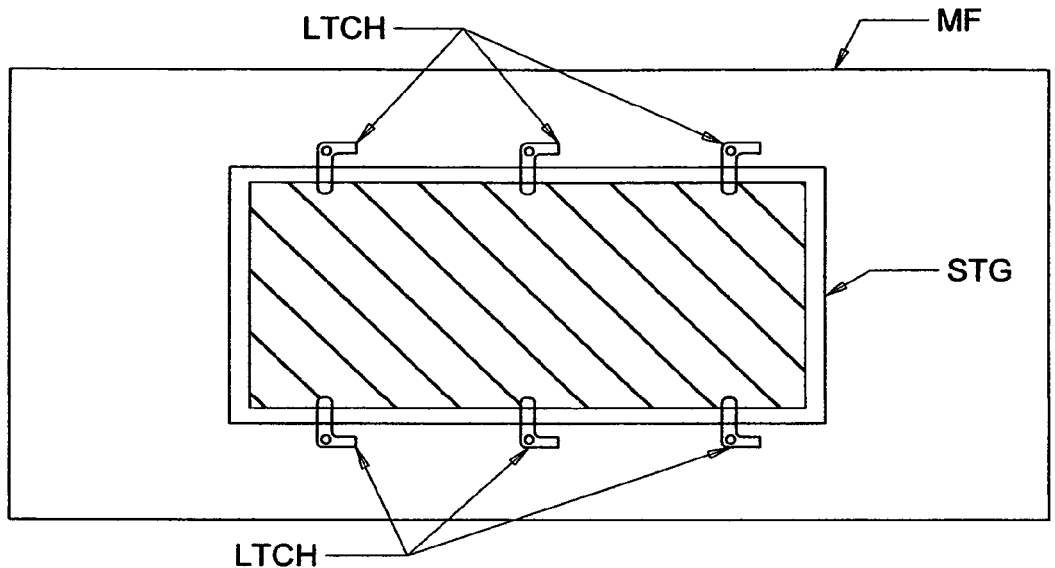
FIGS. 4a, 4b, 4b', 4b" and 4c functionally show that the combination ellipsometer (ES) and alignment (AS) system can be commonly mounted to a mounting frame (MF) to form a sample mapping system, and that reference samples (SSMP) and a protective door can be included.

Turning now to the Drawings, FIG. 1 shows a combination ellipsometer (ES) and alignment (AS) system. The ellipsometer system (ES) is demonstrated as comprising:
  a source of a beam of electromagnetic radiation (ELS);
  a polarizer (P);
  a stage for supporting a sample (SAM/STG);
  an analyzer (A);
  a data detector (DDET); and
  means for adjusting the relative "height" (H) positioning between said stage for supporting a sample (SAM/STG) and, as a unit, said source (ELS) of an ellipsometer beam (EB) of electromagnetic radiation and data detector (DDET); as well as means for translating relative positioning of said sample (SAM/STG) with respect to, as a unit, said source (ELS) of an ellipsometer beam (EB) of electromagnetic radiation and said data detector, along two orthogonal axes; and optionally means for adjusting the relative orientation of the ellipsometer with respect to said sample (SAM/STG) to set the angle (AOI) and plane (POI) of incidence, (see FIG. 3b), of said ellipsometer beam (EB) with respect to a surface of said sample (SAM/STG).

Said ellipsometer system is shown to optionally comprise at least one compensator ((RC) and/or focusing means (CL1) (CL2) CL3) CL4) between said source (ELS) of a beam (EB) of electromagnetic radiation and said data detector (DDET). In use an ellipsometer beam (EB) of electromagnetic radiation from said source (WLS) thereof approaches said sample (SAM/STG) at an oblique angle-of-incidence and reflects therefrom into said data detector (DDET) which produces analyzable data.

FIG. 2a shows that a basic alignment system (AS) comprises:
- an alignment source (ALS) of an alignment beam (AB) of electromagnetic radiation;
- a first alignment beam (AB) focusing means (CLA1) for focusing an alignment beam (AB) of electromagnetic radiation provided from said source thereof onto the sample (SAM/STG) on said ellipsometer system stage (STG) for supporting a sample (SAM);
- a second alignment focusing means (CLA2) for focusing alignment beam electromagnetic radiation which reflects from said sample (SAM) onto a two dimensional detector array (SCRN1); and
- said two dimensional detector array (SCRN1).

In use an alignment beam (AB) of electromagnetic radiation from said alignment source (ALS) thereof is focused onto said sample (SAM) at an oblique angle-of-incidence and reflects therefrom and is focused onto said two dimensional detector array (SCRN1).

FIG. 2b is included to show that beam components reflected from the front (F), and back (B), respectively, sides of the sample (SAM) can form two spots on the two dimensional detector array (SCRN1). The distance between said spots is related to the thickness of the sample (SAM).

FIG. 3a shows that said sample alignment system (AS) preferably further comprises:
- between said second alignment focusing means (CLA2) and said two dimensional detector array (SCRN1) a beam splitter (BS) which diverts a portion of the alignment beam (AB) electromagnetic radiation which reflects from said sample (SAM) to a secondary two dimensional detector array (SCRN2).

Said ellipsometer (ES) and alignment (AS) systems are mounted with respect to one another such that the ellipsometer beam (EB) of electromagnetic radiation and said alignment beam (AB) of electromagnetic radiation impinge on said sample (SAM) at substantially the same location thereupon. FIG. 3b serves to show that the sample (SAM) and stage (STG) might be rotated about orthogonal axes to set (AOI) and POI) of the alignment beam (AB). This should be interpreted to indicate that a functionally equivalent rotational capability can, perhaps alternatively, be provided to the alignment system (AS) and that is relative rotations between the sample (SAM) and alignment system (AL) which is important in the present invention.

FIG. 3c shows that adjusting the height (H) between the sample (SAM) and the alignment system (AS), causes a movement of a spot (HA) on two dimensional detector array (SCRN1). FIG. 3d shows that a relative tip/tilt between the sample (SAM) and the alignment system (AS) causes a spot (TTA) on the secondary two dimensional detector array (SCRN2) to move vertically with (AOI) and horizontally with (POI). Said FIGS. 3c and 3d actually provide specific insight to how the present invention is able to adjust height (H) and (AOI) and (POI) very quickly. Relative height (H) translation and relative (AOI) and (POI) rotations between the stage (STG), (note the stage (STG) is fixed in the FIGS. 4a-4c), and the alignment system (AS) can be performed to position the spots (HA) and (TTA) on two dimensional detector arrays (SCRN1) and (SCRN2) at positions thereon identified as "ideal" (I) therein. The methodology for accomplishing this is described in the Disclosure of the Invention Section of the Disclosure.

Figure 4B:
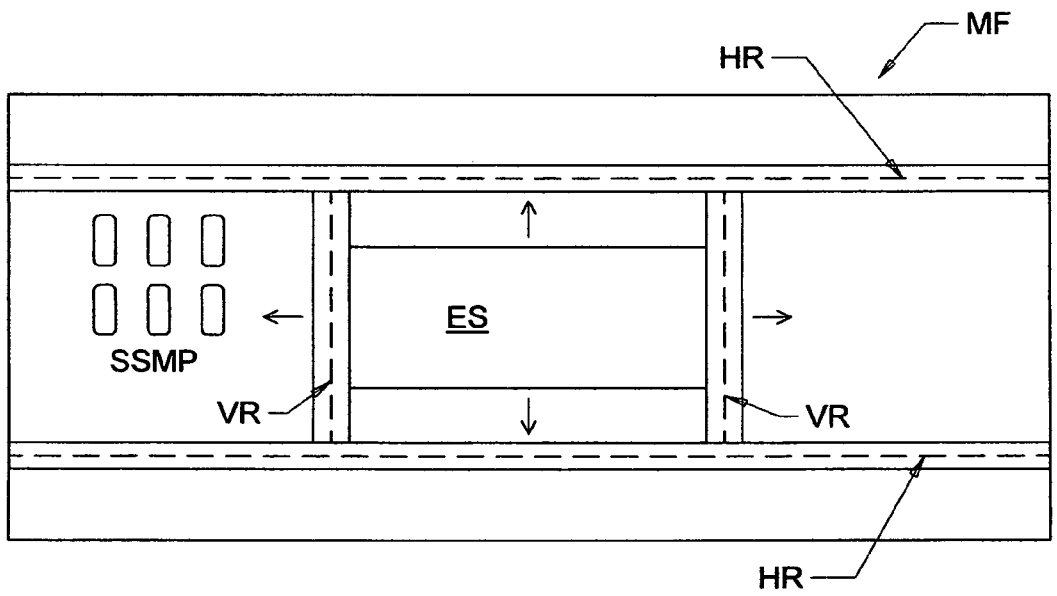
Figure 4C:
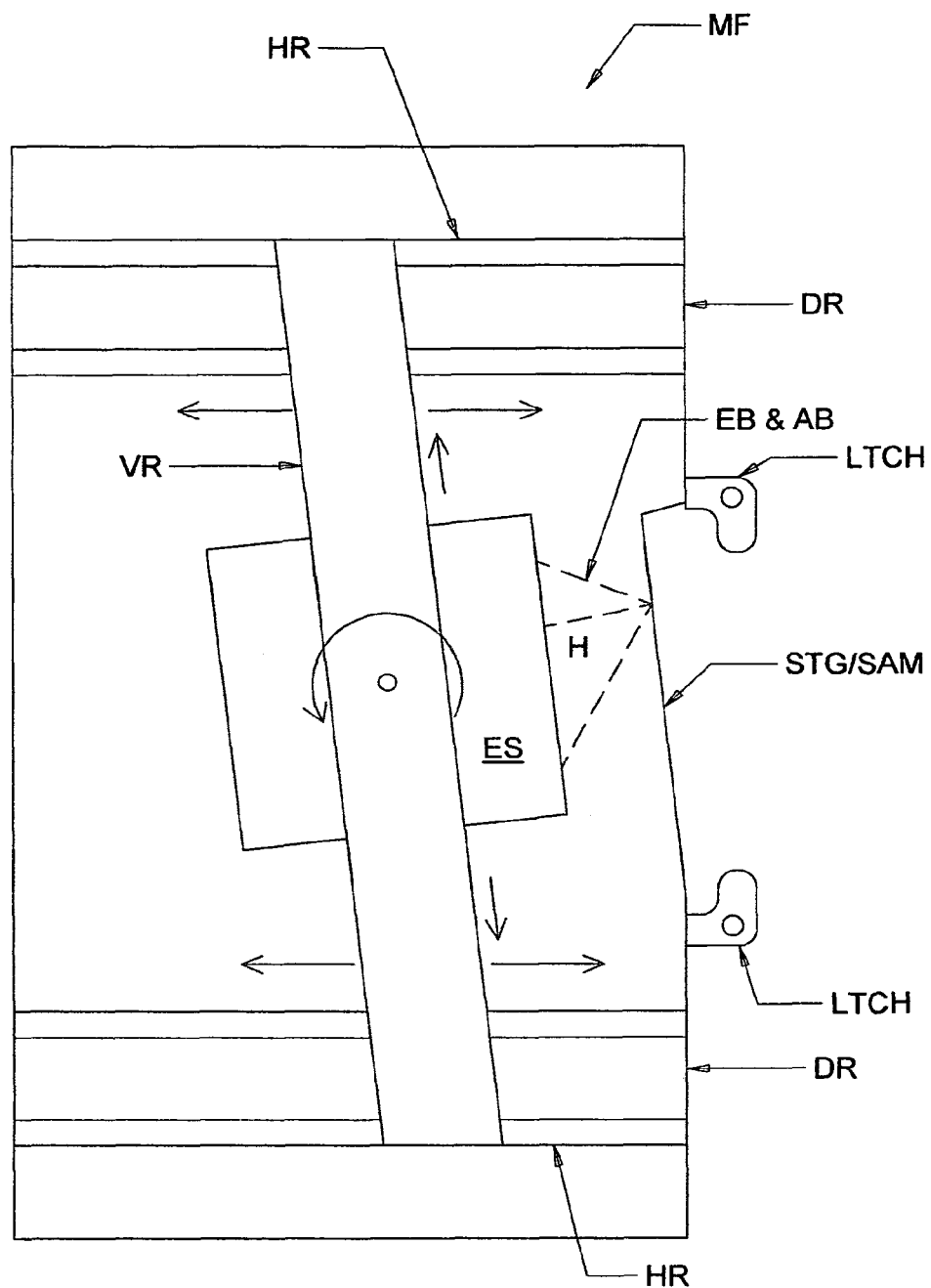
FIGS. 4d-4f show actual embodiment mounting frame (MF), stage (STG) and sample (SAM).

Continuing, FIGS. 4a-4c functionally show that the combination ellipsometer (ES) and alignment (AS) system just described can further comprise:
- a mounting frame (MF) which supports said combination ellipsometer (ES) and alignment (AL) system, said mounting frame (MF) projecting vertically upward from a horizontally oriented support as viewed in elevation. FIG. 4c indicates the presence of means for adjusting the relative "height" (H) positioning between said stage (STG) for supporting a sample (SAM) and, as a unit, said source of a beam of electromagnetic radiation and data detector (collectively indicated by (ES)). A well, said means for translating (HR) (DR) relative positioning of said sample with respect to said source of a beam of electromagnetic radiation and said data detector, along two orthogonal axes. Said optional means for adjusting the relative orientation of the ellipsometer, (indicated by circular arrows), with respect to said sample to set the angle and plane of incidence of said ellipsometric beam with respect to a surface of said sample (SAM).

Further, FIG. 4c shows that said stage (STG) for supporting a sample (SAM) is oriented to secure a sample (SAM) in a plane slightly offset from said vertically upward projected plane of said mounting frame (MF) so that a sample (SAM) entered thereinto does not tend to fall back out thereof, said stage (STG) being of a construction to contact the edges of the sample only, (see FIG. 4a). Also note that a plurality of "clamp means" (LTCH) at the edges of said stage (STG) in FIGS. 4a and 4c, whereat the sample (SAM) contacts said stage (STG). Said clamp means secure the sample (SAM) to the stage (STG) at said edges thereof to better secure said sample (SAM), and to decrease non-planar warping therein. It is noted that sample (SAM) investigated in the present invention can be on the order of a meter or so long along a side and as such can be expected to demonstrate a non-planar surface.

In view of FIGS. 4a-4c, it is disclosed that the present invention can be recast as a sample (SAM) mapping system comprising a mounting frame (MF) which supports a combination ellipsometer (ES) and alignment (AS) system, said mounting frame (MF) projecting substantially vertically upward from a substantially horizontally oriented support, as viewed in elevation, and where said combination ellipsometer (ES) and alignment (AS) system are described above. Also note that FIG. 4b shows the ellipsometer system (ES) can be moved horizontally via a sliding action in guides (HR) or vertically by a sliding action in guides (VR). FIG. 4c indicates guides (DR) allow forward and backward motion which can be applied to adjust (H), (eg. the "height" between the sample (SAM) and the combination (ES). FIG. 4c allows shows that the sample (SAM) is not oriented vertically, but rather is mounted in a fixed position at a slight off-vertical orientation. This is to better secure the sample (SAM). However, achieving that benefit requires that the combination (ES) be rotatable to provide (AOI) and (POI) adjustment capability as shown.

It is noted that FIG. 4b also shows Standard Samples (SSMP) mounted at a location whereat the Ellipsometer system (ES) can cause an incident beam to impinge thereupon. In use, the Ellipsometer system (E) can be positioned to "investigate" a Standard Sample (SSMP) which has known physical and/or optical properties, and the data obtained from the Data Detector (DDET) while the Ellipsometer system (ES) is so positioned can be used to calibrate the Ellipsometer system (ES) via a regression procedure. This calibration approach is described in Patent to Johs et al. U.S. Pat. No. 5,872,630 and basically evaluates parameters in a mathematical model which describe Ellipsometer system (ES) components, in the same way Sample (SAM) parameters are evaluated. FIGS. 4*b*' and 4*b*'' better show the Standard Samples (SSMP), and that Door (D) can be used as protection between uses.

Figure 4D:
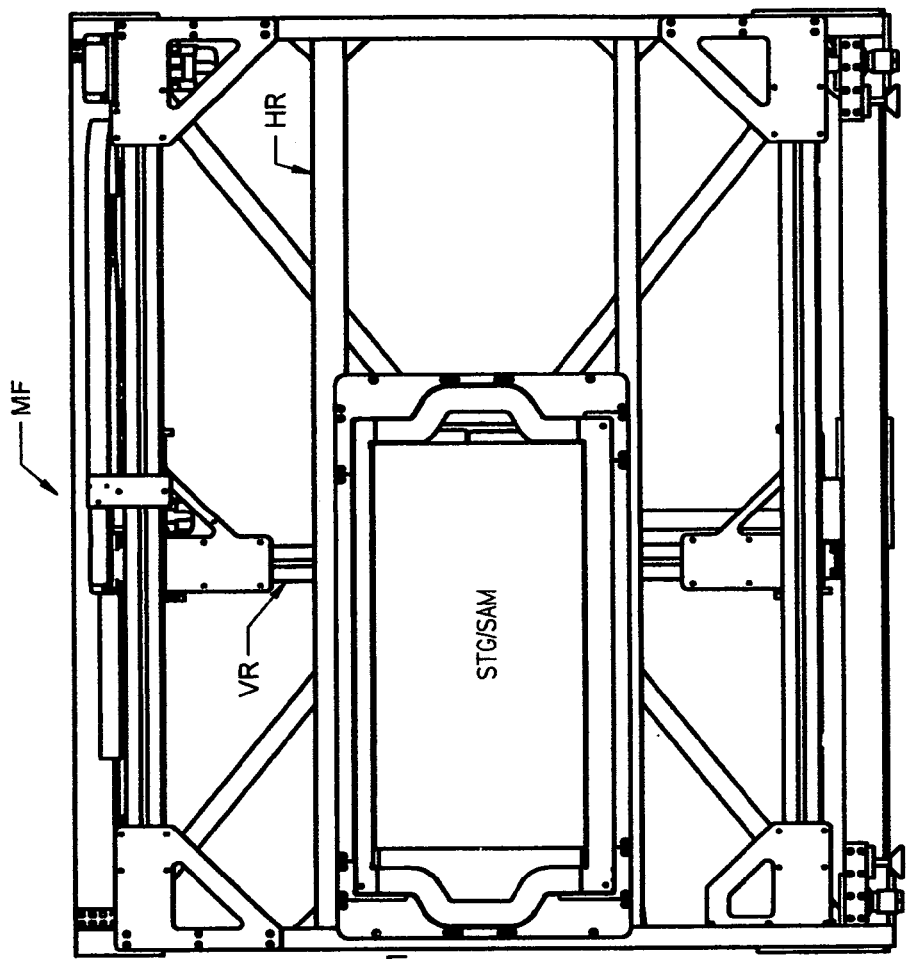
Figure 4E:
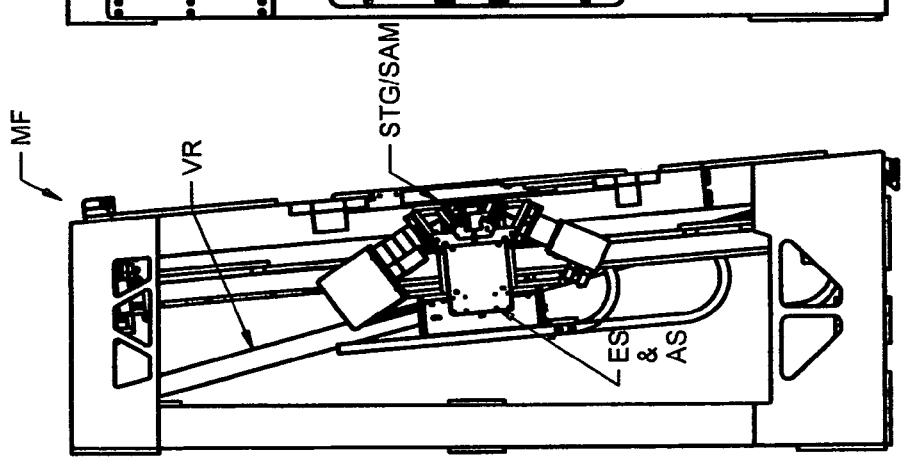
Figure 4F:
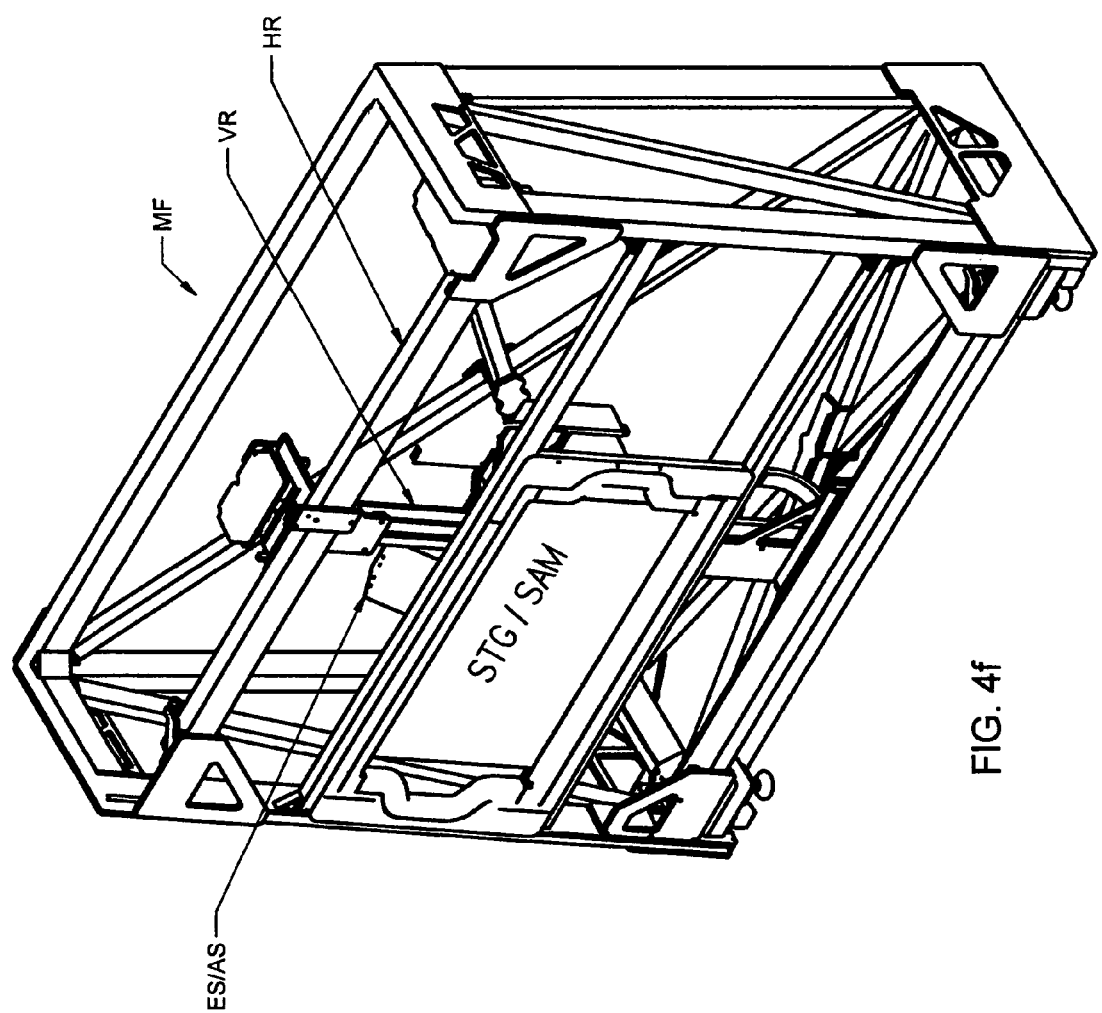

FIGS. 4*d*-4*f* show an actual embodiment mounting frame (MF), stage (STG) and sample (SAM), also showing guides (HR) and (VR) and the location at which the combination ellipsometer (ES) and alignment (AS) system is mounted in the mounting frame (MF), as were functionally indicated in FIGS. 4*a*-4*c*.

It is also noted that the alignment and secondary alignment screens (SCRN1) (SCRN2) can double as means to provide an image of the sample, when an illumination source is added to the alignment system (AS), (not shown). When that is done, as described in Pending application Ser. No. 11/784,750, a relatively large area of the sample surface can be viewed in focus if the relative tilt between the sample (SAM) and the alignment system (AS) is seet to meet the Scheimpflug condition. The 750 Application is included by reference herein.

While the foregoing discussed the very relevant application of an ellipsometer system, the Claims should be broadly considered to include any material system investigation systems such as:
- ellipsometer;
- polarimeter;
- reflectometer;
- spectrophotometer; and
- Mueller Matrix measuring system;

which operate at least one wavelength in at least one wavelength range, such as:
- VUV;
- UV;
- Visible;
- Infrared;
- Far Infrared;
- Radio Wave.

The major difference between an ellipsometer, polarimeter and Mueller Matrix measuring system as compared to a reflectometer or spectrophotometer is that the reflectometer or spectrophotometer does not comprise polarization related elements such as a polarizer (P) and analyzer (A).

Finally, it is noted that the two dimensional detector array (SCRN1) and secondary two dimensional detector array (SCRN2) can be CDD or CMOS Camera etc.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A sample alignment system (AS) in functional combination within a sample investigation system (ES) selected from the group consisting of:
   - ellipsometer;
   - polarimeter;
   - reflectometer;
   - spectrophotometer; and
   - Mueller Matrix measuring system;

said sample investigation system (ES) comprising:
   a source (ELS) of a sample (SAM) investigation beam of electromagnetic radiation;
   a stage (STG) for supporting a sample (SAM);
   a data detector (DDET); and
   means for adjusting the relative "height" positioning between said stage (STG) for supporting a sample (SAM) and, as a unit, said source (ELS) of a sample investigation beam of electromagnetic radiation and data detector (DDET); as well as means for translating relative positioning of said sample (SAM) with respect to said source (ELS) of a sample investigation beam of electromagnetic radiation and said data detector (DDET), along two orthogonal axes, and means for adjusting the relative orientation of the sample investigation system (ES) with respect to said sample (SAM) to set the angle and plane of incidence of said sample (SAM) investigation beam of electromagnetic radiation with respect to a surface of said sample (SAM);

said sample investigation system (ES) optionally comprising at least one polarizer (P), analyzer (A), compensator (RC) and/or focusing means (CL1) (CL2) (CL3) (CL4) between said source (ELS) of a sample (SAM) investigation beam of electromagnetic radiation and said data detector (DDET);

such that in use a sample investigation beam of electromagnetic radiation from said source (ELS) thereof approaches said sample (SAM) at an oblique angle-of-incidence and reflects therefrom into said data detector (DDET); and wherein said alignment system (AS) comprises:
   an alignment source (ALS) of an alignment beam of electromagnetic radiation;
   a first alignment beam focusing means (CLA1) for focusing an alignment beam of electromagnetic radiation provided from said source (ALS) thereof onto a sample (SAM) on said sample investigation system (ES) stage (STG) for supporting a sample (SAM);
   a second alignment focusing means (CLA2) for focusing alignment beam electromagnetic radiation which reflects from said sample onto a two dimensional detector array (SCRN1); and
   said two dimensional detector array (SCRN1);

said sample alignment system (AS) further comprising:
   between said second alignment focusing means (CLA2) and said two dimensional detector array (SCRN1), a beam splitter (BS) which diverts a portion of the alignment beam electromagnetic radiation which reflects from said sample (SAM) to a secondary two dimensional detector array (SCRN2), and said secondary two dimensional detector array (SCRN2);

such that in use an alignment beam of electromagnetic radiation from said source (ALS) thereof is focused onto said sample (SAM) at an oblique angle-of-incidence and reflects therefrom and is focused onto said two dimensional detector array (SCRN1) with a portion thereof being directed to secondary two dimensional detector array (SCRN2) via beam splitter (BS);

said sample (SAM) investigation system (ES) and alignment system (AS) being mounted with respect to one another such that the sample investigation beam of electromagnetic radiation and said alignment beam of electromagnetic radiation impinge on said sample (SAM) at substantially the same location;

such that in use, while monitoring two dimensional detector array (SCRN1), causing an alignment beam of electromagnetic radiation from said source (ALS) thereof to be focused onto said sample (SAM) at an oblique angle-of-incidence, reflect therefrom and become focused onto said two dimensional detector array (SCRN1), adjusting the means for adjusting the relative "height" positioning between said stage (STG) for supporting a sample until the location at which the alignment beam arrives thereat is at an aligned position thereupon;
and
such that in use the means for adjusting the relative orientation of the sample investigation system (ES) with respect to said sample (SAM), to set the angle and plane of incidence of said beam with respect to a surface of said sample (SAM) until said alignment beam reflected from said sample (SAM) surface appears on the two dimensional detector array (SCRN2) an aligned position thereupon.

2. A sample alignment system as in claim 1, which further comprises at least one known standard sample (SSMP) positioned away from said stage (STG) for supporting a sample (SAM), such that in use the sample investigation system (ES) and sample alignment system (AS) are positioned so that electromagnetic beams from each are directed to intereact with said at least one known standard sample (SSMP) while data is acquired from at least the sample investigation system (ES), followed by using said data to calibrate said sample investigation system (ES).

3. A sample alignment system as in claim 1, which further comprises a door (D) which is applied to cover said at least one known standard sample (SSMP) when it is not in use, to prevent contamination thereof.

4. A method of investigating a plurality of locations on a sample comprising the steps of:
   a) providing a sample alignment system (AS) in functional combination within a sample investigation system (ES) selected from the group consisting of:
      ellipsometer;
      polarimeter;
      reflectometer;
      spectrophotometer; and
      Mueller Matrix measuring system;
   said sample investigation system (ES) comprising:
      a source (ELS) of a sample (SAM) investigation beam of electromagnetic radiation;
      a stage (STG) for supporting a sample (SAM);
      a data detector (DDET); and
      means for adjusting the relative "height" positioning between said stage (STG) for supporting a sample (SAM) and, as a unit, said source (ELS) of a sample investigation beam of electromagnetic radiation and data detector (DDET); as well as means for translating relative positioning of said sample (SAM) with respect to said source (ELS) of a sample investigation beam of electromagnetic radiation and said data detector (DDET), along two orthogonal axes, and means for adjusting the relative orientation of the sample investigation system (ES) with respect to said sample (SAM) to set the angle and plane of incidence of said sample (SAM) investigation beam of electromagnetic radiation with respect to a surface of said sample (SAM);
   said sample investigation system (ES) optionally comprising at least one polarizer (P), analyzer (A), compensator (RC) and/or focusing means (CL1) (CL2) (CL3) (CL4) between said source (ELS) of a sample (SAM) investigation beam of electromagnetic radiation and said data detector (DDET);
   such that in use a sample investigation beam of electromagnetic radiation from said source (ELS) thereof approaches said sample (SAM) at an oblique angle-of-incidence and reflects therefrom into said data detector (DDET); and
   wherein said alignment system (AS) comprises:
      an alignment source (ALS) of an alignment beam of electromagnetic radiation;
      a first alignment beam focusing means (CLA1) for focusing an alignment beam of electromagnetic radiation provided from said source (ALS) thereof onto a sample (SAM) on said sample investigation system (ES) stage (STG) for supporting a sample (SAM);
      a second alignment focusing means (CLA2) for focusing alignment beam electromagnetic radiation which reflects from said sample onto a two dimensional detector array (SCRN1); and
      said two dimensional detector array (SCRN1);
   said sample alignment system (AS) further comprising:
      between said second alignment focusing means (CLA2) and said two dimensional detector array (SCRN1), a beam splitter (BS) which diverts a portion of the alignment beam electromagnetic radiation which reflects from said sample (SAM) to a secondary two dimensional detector array (SCRN2), and said secondary two dimensional detector array (SCRN2);
   such that in use an alignment beam of electromagnetic radiation from said source (ALS) thereof is focused onto said sample (SAM) at an oblique angle-of-incidence and reflects therefrom and is focused onto said two dimensional detector array (SCRN1) with a portion thereof being directed to secondary two dimensional detector array (SCRN2) via beam splitter (BS);
   said alignment system (AS) further comprising at least one known standard sample (SSMP) positioned away from said stage (STG) for supporting a sample (SAM);
   said sample (SAM) investigation system (ES) and alignment system (AS) being mounted with respect to one another such that the sample investigation beam of electromagnetic radiation and said alignment beam of electromagnetic radiation impinge on said sample (SAM) at substantially the same location;
   such that in use, while monitoring two dimensional detector array (SCRN1), causing an alignment beam of electromagnetic radiation from said source (ALS) thereof to be focused onto said sample (SAM) at an oblique angle-of-incidence, reflect therefrom and become focused onto said two dimensional detector array (SCRN1), adjusting the means for adjusting the relative "height" positioning between said stage (STG) for supporting a sample until the location at which the alignment beam arrives thereat is at an aligned position thereupon;
   and
   such that in use the means for adjusting the relative orientation of the sample investigation system (ES) with respect to said sample (SAM), to set the angle and plane of incidence of said beam with respect to a surface of said sample (SAM) until said alignment beam reflected from said sample (SAM) surface appears on the two dimensional detector array (SCRN2) an aligned position thereupon;
   b) causing the sample investigation system (ES) and sample alignment system (AS) to be positioned such that electromagnetic beams from each are directed to intereact with said at least one known standard sample (SSMP) while data is acquired from at least the sample investigation system (ES), followed by using said data to calibrate said sample investigation system (ES);
   c) causing the sample investigation system (ES) and sample alignment system (AS) to be positioned such that electromagnetic beams from each are directed to intereact with a location on said sample (SAM) such that alignment beam of electromagnetic radiation from said source (ALS) of the sample alignment system is focused onto said sample (SAM) location at an oblique angle-of-incidence, reflects therefrom and is focused onto said two dimensional detector array (SCRN1) with a portion thereof being directed to secondary two dimensional detector array (SCRN2) via beam splitter (BS), followed by using information derived from screens (SCRN1) and (SCRN2), to adjust the distance between the sample (SAM) and said source (ELS) of a sample investigation beam of electromagnetic radiation and said data detector (DDET) as a unit, and to adjust the angle and plane of incidence of said sample (SAM) investigation beam of electromagnetic radiation with respect to a surface of said sample (SAM);

d) acquiring data from said data detector (DDET) and therefrom deriving sample (SAM) characterizing information therefrom; and e) repeating steps c and d a plurality of times to provide (SAM) characterizing information at a plurality of locations thereupon.

5. A method of aligning a sample in an ellipsometer system, which ellipsometer system comprises:
  a source of a beam of electromagnetic radiation;
  a polarizer;
  a stage for supporting a sample;
  an analyzer;
  a data detector;
  means for adjusting the relative "height" positioning between said stage for supporting a sample and, as a unit, said source of a beam of electromagnetic radiation and data detector; as well as means for translating relative positioning of said sample with respect to said source of an ellipsometer beam of electromagnetic radiation and said data detector, along two orthogonal axes, and optionally means for adjusting the relative orientation of the ellipsometer systems with respect to said sample to set the angle and plane of incidence of said ellipsometer beam with respect to a surface of said sample;

said ellipsometer system optionally comprising at least one compensator and/or focusing means between said source of a beam of electromagnetic radiation and said data detector;

such that in use a beam of electromagnetic radiation from said source thereof approaches said sample at an oblique angle-of-incidence and reflects therefrom into said data detector;

said method comprising the steps of:
  a) functionally mounting a sample alignment system to said ellipsometer system, which sample alignment system comprises:
    an alignment source of an alignment beam of electromagnetic radiation;
    a first alignment beam focusing means for focusing an alignment beam of electromagnetic radiation provided from said source thereof onto a sample on said ellipsometer system stage for supporting a sample;
    a second alignment focusing means for focusing alignment beam electromagnetic radiation which reflects from said sample onto a two dimensional detector array; and
    said two dimensional detector array;
  such that in use an alignment beam of electromagnetic radiation from said source thereof is focused onto said sample at an oblique angle-of-incidence and reflects therefrom and is focused onto said two dimensional detector array;

said sample alignment system optionally further comprising:
  between said second alignment focusing means and said two dimensional detector array a beam splitter which diverts a portion of the alignment beam electromagnetic radiation which reflects from said sample to a secondary two dimensional detector array, and said secondary two dimensional detector array;

said ellipsometer and alignment system being mounted with respect to one another such that the ellipsometer beam of electromagnetic radiation and said alignment beam of electromagnetic radiation impinge on said sample at substantially the same location;

said method further comprising:
prior to step e, performing steps b and c at least once, in which steps b and c are:
  b) while monitoring output intensity from said data detector causing a beam of electromagnetic radiation from said source thereof to approach said sample at an oblique angle-of-incidence and reflect therefrom into said data detector, adjusting the means for adjusting the relative "height" positioning between said stage for supporting a sample, and, as a unit, said source of a beam of electromagnetic radiation and data detector, until output from said data detector is of a desirable intensity; and
  c) causing the source of an alignment beam of electromagnetic radiation from said source thereof to approach said sample at an oblique angle-of-incidence and reflect therefrom onto said two dimensional detector array and identifying the location on said two dimensional detector array as an aligned position;

said method further comprising performing steps d, e and f a plurality of times, wherein steps d, e and f are:
  d) using said means for translating relative positioning of said sample with respect to, as a unit, said source of an ellipsometer beam of electromagnetic radiation and said data detector, along two orthogonal axes, causing relative translation of said sample along at least one of said orthogonal axes so that a new spot on said sample is investigated by said ellipsometer beam, and such that the location at which the alignment beam reflected from said sample surface in step c appears on the two dimensional detector array, possibly at a different location than said aligned position;
  e) if necessary, adjusting the means for adjusting the relative "height" positioning between said stage for supporting a sample and, as a unit, said source of a beam of electromagnetic radiation and data detector, until said alignment beam reflected from said sample surface in step c appears on the two dimensional detector array at said aligned position;
  f) with the above adjustment set, acquiring ellipsometric data from said data detector.

6. A method as in claim 5, in which the which the ellipsometer system further comprises at least one known standard sample (SSMP) positioned away from said stage (STG) for supporting a sample (SAM), such that in use the sample investigation system (ES) and sample alignment system (AS) are positioned so that electromagnetic beams from each are directed to intereact with said at least one known standard sample (SSMP) while data is acquired from at least the sample investigation system (ES), followed by using said data to calibrate said sample investigation system (ES).

7. A method as in claim 6, which further comprises a door (D) which is applied to cover said at least one known standard sample (SSMP) when it is not in use, to prevent contamination thereof.

* * * * *